United States Patent
Mason et al.

(10) Patent No.: US 6,832,506 B1
(45) Date of Patent: Dec. 21, 2004

(54) APPARATUS AND METHOD FOR MEASURING A PROPERTY OF A LIQUID

(76) Inventors: Julian Mason, 50 Aveline Street, Kennington, London (GB), SE11 5DQ; Andy Augousti, 23 West Green, Yateley Hampshire, Surrey (GB), GU46 7RW; Norman McMillan, Craiguecullen, Carlow, County Carlow (IE); Stuart Smith, Baltyboys, Blessington, County Wicklow (IE); Michael Baker, Chapelstown, Carlow, County Carlow (IE)

(*) Notice: Subject to any disclaimer, the term of this patent is extended or adjusted under 35 U.S.C. 154(b) by 0 days.

(21) Appl. No.: 10/130,403
(22) PCT Filed: Nov. 16, 2000
(86) PCT No.: PCT/IE00/00148
§ 371 (c)(1), (2), (4) Date: Sep. 23, 2002
(87) PCT Pub. No.: WO01/36959
PCT Pub. Date: May 25, 2001

(30) Foreign Application Priority Data
Nov. 16, 1999 (IE) ................................................ S990960

(51) Int. Cl.⁷ .............................................. G01N 29/00
(52) U.S. Cl. ........................................ 73/64.53; 73/590
(58) Field of Search ................................. 73/64.53, 579, 73/589, 590, 54.02, 54.01

(56) References Cited

U.S. PATENT DOCUMENTS

| 4,391,129 | A | * | 7/1983 | Trinh et al. ................. 73/64.48 |
| 4,788,466 | A | * | 11/1988 | Paul et al. ............. 310/323.06 |
| 5,422,664 | A | * | 6/1995 | Stephany ...................... 347/14 |
| 5,739,432 | A | * | 4/1998 | Sinha ........................... 73/579 |
| 6,003,388 | A | * | 12/1999 | Oeftering ................. 73/864.01 |
| 6,370,939 | B2 | * | 4/2002 | Smith et al. ................ 73/19.03 |
| 6,647,764 | B1 | * | 11/2003 | Paul et al. .................. 73/54.41 |

FOREIGN PATENT DOCUMENTS

JP  02098651 A  *  4/1990  ........... G01N/11/00

* cited by examiner

Primary Examiner—Charles D. Garber
(74) Attorney, Agent, or Firm—Whiteford, Taylor & Preston LLP; Jeffrey C. Maynard; Gregory M. Stone

(57) ABSTRACT

An apparatus for use in characterising liquids by obtaining a fingerprint of the liquid. This allows one to measure a property of a liquid, and thereby distinguish between liquids. The apparatus comprises means for directing acoustic energy at a sample of the liquid, which is preferably in the form of a drop, and means for deriving a signal related to the interaction of the acoustic energy with the liquid sample. The drop may change in volume or shape during the measurements, to derive additional properties of the liquid. The apparatus and method of the invention are used in distinguishing and analysing a variety of liquid samples.

23 Claims, 5 Drawing Sheets

APPARATUS AND METHOD FOR MEASURING A PROPERTY OF A LIQUID

Figure 1:
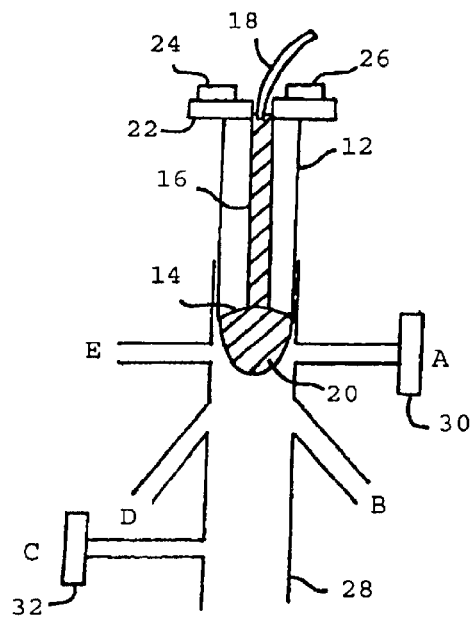

This invention relates to an apparatus and method for measuring a property of a liquid. More particularly, it relates to the characterisation of liquids by obtaining fingerprints for the liquids, from which various properties can be derived.

There is a need for a range of techniques to analyse liquids to detect differences between samples, such as in quality control, detection of counterfeit goods, or analysis of tampering. The invention also has as its aim the provision of an improved technique for use in forensic analysis of liquids.

According to the present invention there is provided an apparatus for use in measuring a property of a liquid comprising means for directing acoustic energy at a sample of the liquid, and means for deriving a signal related to the interaction of the acoustic energy with the liquid sample.

The invention further provides a method for measuring a property of a liquid comprising directing acoustic energy at a sample of the liquid, deriving a signal related to the interaction of the acoustic energy with the liquid sample, and determining a property of the liquid based upon the said signal.

The liquid, which is preferably in the form of a drop, may be a pure liquid, a mixture of liquids, a solution of a solid substance, a suspension of a solid within a liquid or a colloidal suspension, and the term "liquid" is used herein to signify all of these possibilities.

The term "drop", as used herein, is defined as the interface that is formed between a liquid and any other material or materials, such as a solid, gas or liquid, under the force of the surface tension of the interface usually, but not always, combined with the force of gravity, acting on a particular geometrical arrangement of said liquid and materials.

The drop can be formed using bioactive agents or radio-active material.

The drop can undergo one or more phase changes during or at a particular point in its growth cycle, and it can be contaminated by, or dissolved, or evaporated into a surrounding medium.

Acoustic energy may be launched at the liquid sample from one or more sources, and the signal produced by the interaction with the sample can be obtained by various methods. One method is by examination of the loading effect on the driving signal to the acoustic source(s). A second is by comparing the driving signal to the modulated signal received by one or more detectors. The formation of the drop can take place directly upon an acoustic source or at the end of an acoustic guide attached to a source and/or a detector. Both configurations will henceforth be referred to as an "acoustic drop head". The drop head can be arranged to form either pendant or sessile drops.

The drop formed at the end of the acoustic drop head can be analysed statically for a fixed drop volume or dynamically during its growth and release cycle, where one or more of a succession of drops are allowed to drip from the end of the acoustic drop head. Thus one may analyse small volumes, or continuously monitor a liquid by bleeding off sample droplets for analysis. The liquid may also be allowed to evaporate from the drop formed under both static or dynamic drop conditions.

The acoustic energy may be any acoustic radiation that can be coupled into the drop, and it can be pulsed, continuous, varying in frequency, amplitude or phase or otherwise modulated to facilitate the particular analysis being performed. The acoustic energy can be coupled directly into the drop using the acoustic drop head, which is in direct contact with the test liquid or alternatively it can be launched at the unattached surface of the drop through a medium of different acoustic impedance. In such a case one may monitor two or more signals—one is the signal that penetrates the drop, and the other is based on the acoustic field set up immediately outside of the drop. In some embodiments the source transducer may also act as the detector transducer.

The signal related to the interaction of the acoustic energy and the liquid sample can be measured using an acoustic transduction measurement system. Any change in the driving signal from the acoustic radiator and the modulated signal is then used to deduce properties relating to the liquid under examination. The changes in the electrical driving signal referred to above may arise from variations in the acoustic impedance or geometry of the test liquid, thereby "loading" the signal produced by the source transducer. Changes in the acoustic signal may affect amplitude, phase, frequency, reverberation time, harmonics etc.

The invention can be used to measure indirectly the following properties of a liquid:

Surface Tension

Viscosity

Acoustic Impedance (i.e. density and the speed of sound within the test liquid).

From these measurements, other properties of the test liquid ban be determined, such as the concentration level of other species contained within the liquid.

The acoustic energy may be optimised in terms of frequency and power to set the drop of liquid into oscillation. Devices that monitor the oscillation of the drop that is energised in this fashion and simultaneously or subsequently monitor the drop by its acoustic signal as described above are within the scope of this invention. In addition, the invention includes the acoustic analysis of drops that are stimulated into oscillation or movement by any other means, such as mechanical energy, acoustic energy, an external force, thermal energy or as the result of a chemical or biological reaction Embodiments of this invention are also possible where the surface of the sample liquid is not a drop, but rather forms the meniscus of a liquid within a tube, preferably a capillary tube.

Embodiments of the invention will now be described, by way of example, with reference to the accompanying drawings, in which:

FIG. 1 is a schematic diagram of an apparatus for performing the invention; and

FIGS. 2(a) to 2(d) illustrate alternative arrangements both for launching acoustic energy at the drop and also the positioning of detectors.

Figure 3:
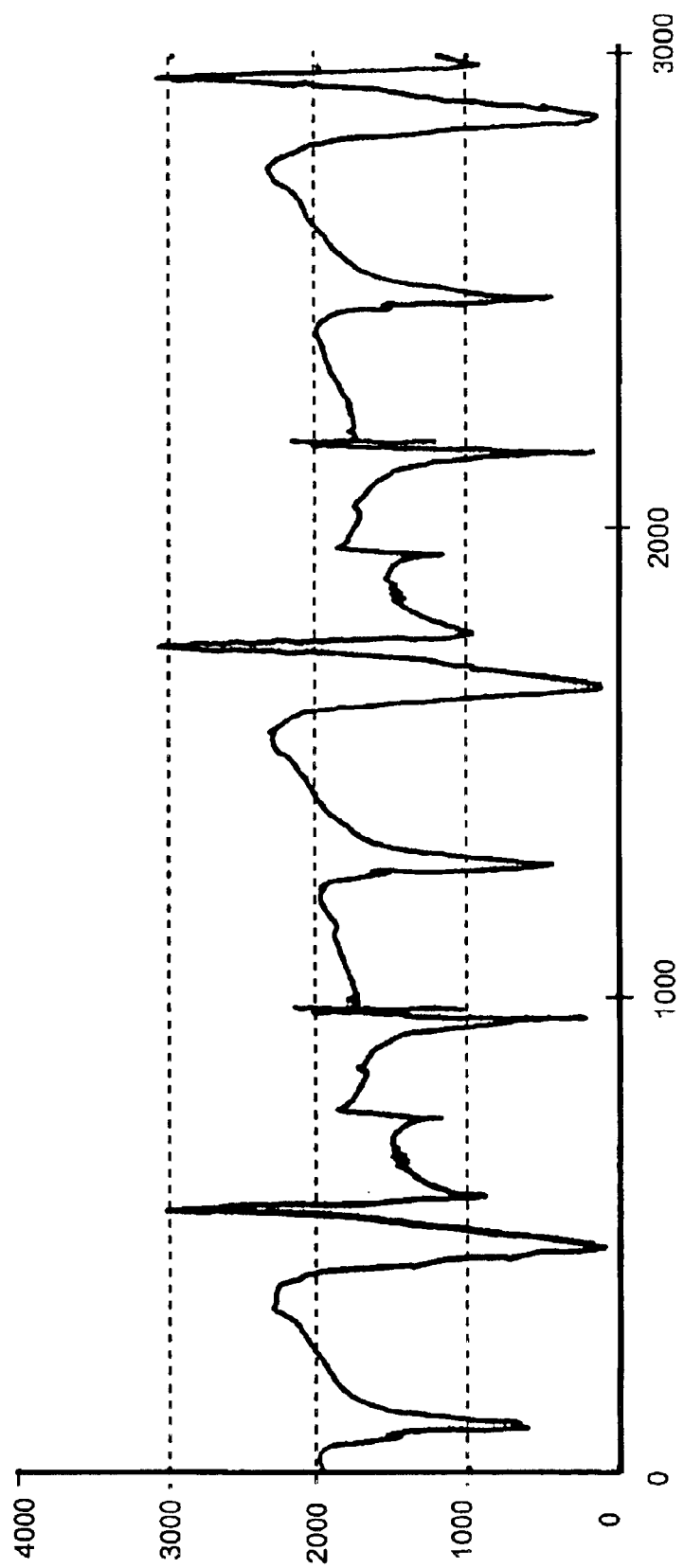
Figure 4:
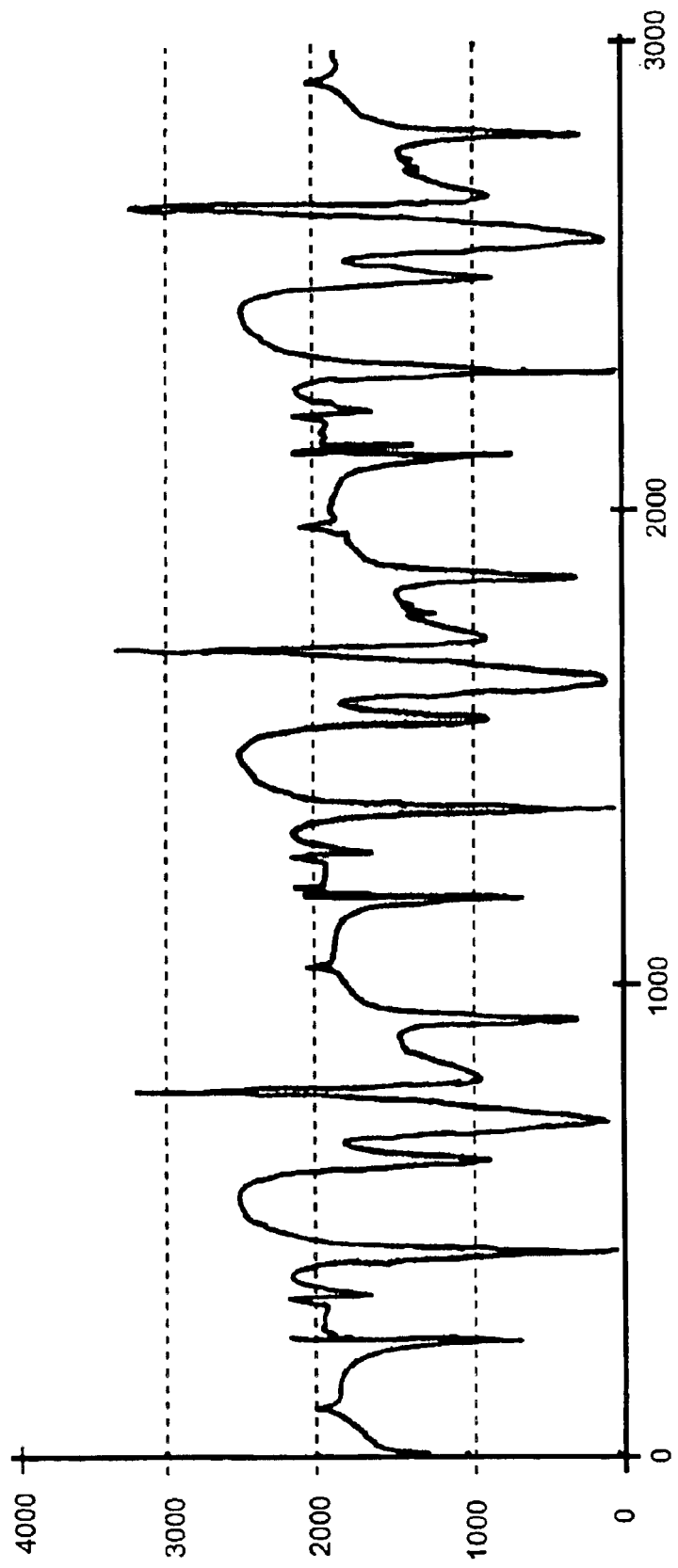
Figure 5:
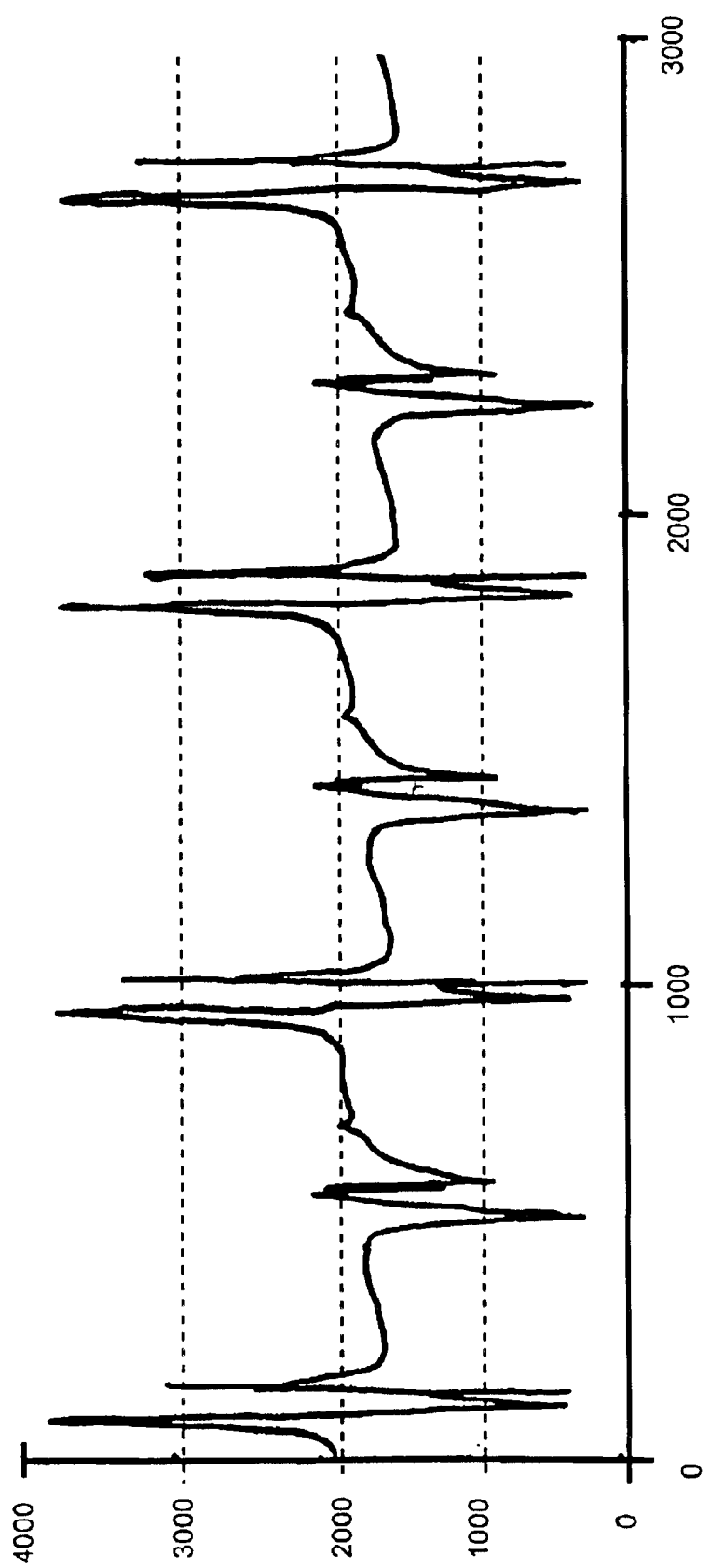
Figure 6:
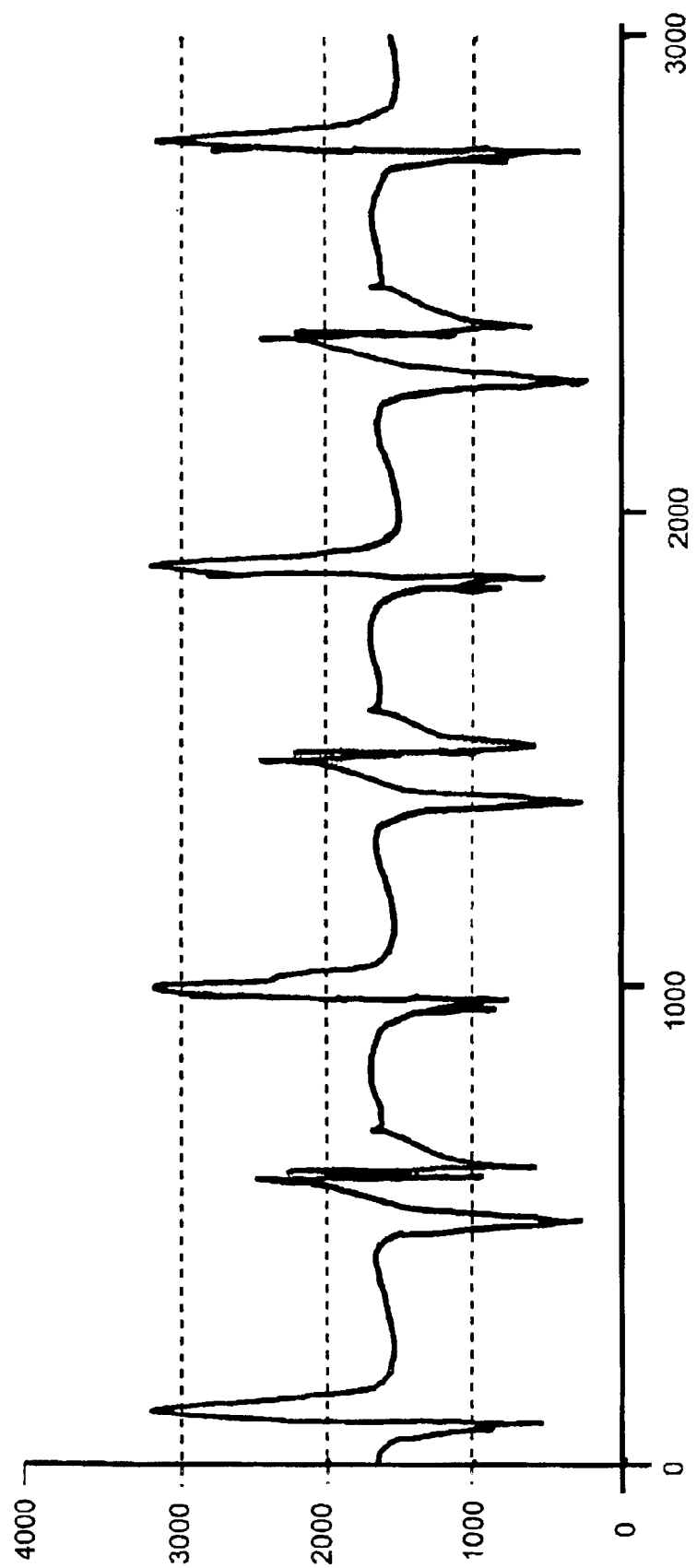

FIGS. 3 and 4 are the fingerprints derived using a method of the invention in respect of two cola soft drinks; and FIGS. 5 and 6 are the fingerprints derived using a method of the invention in respect of two lagers.

In the figures the same reference numerals have been used for the same or equivalent features.

Referring to FIG. 1, an acoustic drop head 10 includes a cylindrical body 12 orientated with its axis substantially vertical. The body 12 has a concave lower surface 14 and a central axial bore 16 opening onto the surface 14. A liquid sample is delivered to the acoustic drop head via a tube 18 communicating with the bore 16, so that the liquid forms a pendant drop 20. The delivery of the liquid can be via syringe, pump or using a constant head of pressure, e.g. from a reservoir. Thus the drop 20 may be static or it may be one of a succession of drops falling intermittently from the body 12. The bore 16 in the body 12 can be in any position provided there is a route to the drop-forming surface 14. The cross-sectional profile of the drop-forming surface 14 is contoured to ensure repeatable drop shapes and drop dimensions.

The drop head 10 also includes a disc 22 at the top of, and having a greater diameter than, the body 12. The disc 22 is in intimate contact with or is integral with, the body 12, and provides support for an acoustic source 24 and an acoustic detector 26. In use, acoustic energy from the source 24 is coupled into the drop head 10 and travels through the body 12 and into the drop 20. The combination of drop head shape and drop geometry modulates the acoustic signal which is then monitored by the detector 26 to provide a corresponding signal.

As seen in FIG. 1, the lower end of body 12 is disposed coaxially within the upper end of a vertical tube 28, the latter having various side branches A to E which may be normal to the axis of the tube (branches A, C, E) or inclined thereto (branches B, D). The acoustic energy from a further source 30 (which can be positioned at the end of branch A or B) is used to couple energy both into the drop 20 and into the medium surrounding it. The modulated signal can then be detected by a second detector 32 located at any of branches C, D or E. In addition to this, the driving signal to the acoustic sources 24, 30 is also monitored as this can be modulated by the geometry of the drop 20. Detector 32 can also be used to determine the acoustic energy radiating out of the drop from source 24.

In general there may be one or more acoustic sources each disposed, like the source 26, on the drop head 10 itself or, like the source 30, spaced therefrom, and also one or more acoustic detectors likewise disposed on the drop head or spaced therefrom.

The drive frequency to the acoustic source(s) may be varied over a wide range, from tens of kilohertz to a few megahertz. The electrical signal from the detector(s) is then plotted against time to produce a graph called a tensiogram. The features in the tensiogram are then used to determine the properties of the liquid.

Figure 2A:
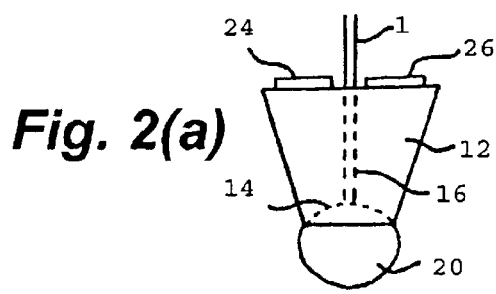
Figure 2B:
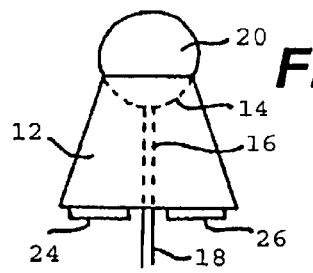
Figure 2C:
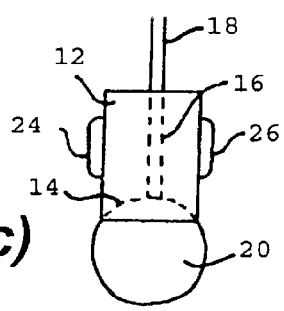
Figure 2D:
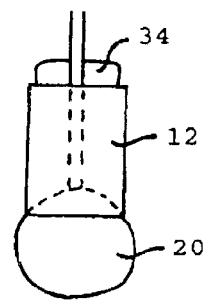

FIGS. 2(a) to 2(d) illustrate alternative arrangements both for launching acoustic energy at the drop and also the positioning of detectors. In FIG. 2(a), the body 12 of the drop head is generally in the form of a truncated cone, thereby dispensing with the need for the disc 22 (FIG. 1). FIG. 2(b) shows the same arrangement inverted to form a sessile drop 20. FIG. 2(c) shows the source 24 and detector 26 on opposite sides of the body 12, while FIG. 2(d) uses a combined acoustic source/detector 34. The drop heads of FIGS. 2(c) and 2(d) may also be inverted to produce sessile drops.

Other embodiments of the device include those where the foregoing acoustic method of analysis of a liquid is combined with other methods, such as optical analysis and capacitance-based techniques that have been described elsewhere in work published by the present applicants.

The invention can be used both for measuring the mechanical and chemical properties of a liquid as detailed above, but also for identification of an unknown liquid. Examples of applications of such measurements will include on-line quality control measurements, detection of fake materials, biomedical fluid measurements, and reverse synthesis of particular formulations, es well as any other are measurements on liquids are involved.

EXAMPLE

Experimental arrangement and procedure used to obtain characteristic output data (fingerprints) for soft drinks and beers.

The acoustic drop head used in this Example was designed to produce pendant drops using the configuration in FIG. 1 (with the omission of vertical tube 28 and its appendages) which was manufactured out of a single section of brass. It was machined to produce a disc section at the top (25 mm in diameter and 1.5 mm thick) and a cylindrical shaft at the bottom (9 mm in diameter and 30 mm in length). A domed recess was machined into the bottom end of the cylindrical shaft to ensure proper wetting of the drop formation surface.

A 2 mm diameter hole which acted as a fluid delivery passageway was drilled through the axis of the probe head from the top of the disk to the bottom of the shaft. Two ultrasonic transducers (10 mm in diameter and 1 mm thick with an operating range from 20 KHz to 1 MHz) were soldered to the disk section by one of their metallised end faces.

The centres of the transducers were 6.5 mm from the disk axis and they were aligned such that the axes of both transducers and the fluid passageway were parallel and coplanar. Since the end face of each transducer was soldered directly to the brass disk this not only provided a good acoustic coupling but also provided a common electrical ground contact.

Test liquid was poured into a constant head tank, which then flowed through 2 mm plastic tubing (with a 0.9 mm bore) to the acoustic drop head. The plastic tube was inserted into the fluid passageway of the probe head to the depth of 5 mm to provide a fluid tight connection. The remaining face/electrical contact of the source transducer was soldered to a lead connected to a Farnell signal generator which had a frequency range from DC to 1 MHz. The remaining face/electrical contact surface of the detector was used as an input to an op-amp where the signal was both amplified and rectified. The resulting DC signal was then applied to a 12 bit ADC to permit data logging.

All liquids were degassed and allowed to reach room temperature before being poured in to the header tank. Between each test tap water was flushed through the system. After flushing, test liquid was allowed to flow until equilibrium in the system was reached.

This particular embodiment of this device was operated at a frequency of 518,609 Hz and was used to test a number of liquids and liquid mixtures. It was found that the device output was extremely sensitive to variations in drop head geometry, orientation, temperature, ultrasonic frequency and fluid flow rate, so close environmental control and controlled fluid delivery is required to achieve reproducible results.

FIGS. 3 and 4 show sample results obtained for the two cola drinks Coca Cola (Trade Mark) and Diet Pepsi (Trade Mark) respectively. The x and y axes are plotted with arbitrary units here, but by way of scaling, a single drop took approximately 110 seconds to form. The plots are both heavily featured, which is helpful for the purposes of characterisation, since a greater number of features means that there is more scope for variation from one liquid to another.

Although the flow rates are slightly different, both plots illustrate the repeatability of measurement within a particular measurement run, with several complete drop growth cycles being visible for each plot. The difference between the two traces is very marked, and indeed this should be contrasted shortly with FIGS. 5 and 6 for Heineken (Trade Mark) lager and Hofineister (Trade Mark) lager respectively, which are very different from these and each other in turn.

The largest factor in causing the variation between the Diet Pepsi and the Coca Cola responses is the difference in the levels of sugar. There are many peaks and troughs in each plot, and the difference between the two is very marked.

FIGS. 5 and 6 show patterns which are generally different to those of FIGS. 3 and 4, but are in some ways similar to one another, and are perhaps indicative of a "lager" profile. However, the relative depth and position of the peaks and troughs is quite different between FIGS. 5 and 6, with some peaks that are present in the Hofmeister plot being absent in the corresponding plot for Heineken.

The invention is not limited to the embodiments described herein which may be modified or varied without departing from the scope of the invention.

What is claimed is:

1. An apparatus for use in measuring a property of a liquid comprising means for directing acoustic energy at a sample of the liquid, an acoustic modulator for modulating the acoustic energy independently of the resonant frequency of the sample, means for deriving a signal related to the interaction of the acoustic energy with the liquid sample as the acoustic energy is modulated, and output means for providing an output based on said derived signal, wherein the liquid sample is in the form of a drop which is analysed dynamically during a change in drop volume, whereby the output provides a characteristic measurement of the properties of the liquid over a range of volumes based on varying acoustic energy input parameters.

2. An apparatus according to claim 1, wherein the drop is formed directly upon the means for directing acoustic energy at the sample.

3. An apparatus according to claim 2, wherein the means for directing acoustic energy comprises an acoustic source.

4. An apparatus according to claim 2, wherein the means for directing acoustic energy comprises an acoustic guide attached to an acoustic source, the drop being formed on an end of the acoustic guide.

5. An apparatus according to claim 1, wherein the means for deriving a signal related to the interaction of the acoustic energy with the liquid sample comprises an acoustic detector, and wherein the drop is formed directly upon the detector.

6. An apparatus according to claim 1, wherein the means for deriving a signal related to the interaction of the acoustic energy with the liquid sample comprises an acoustic detector having an acoustic guide attached thereto, and wherein the drop is formed directly upon an end of the guide.

7. An apparatus according to claim 1, wherein the liquid sample is arranged to form pendant drops.

8. An apparatus according to claim 1, wherein the liquid sample is arranged to form sessile drops.

9. An apparatus according to claim 1, wherein the means for directing acoustic energy comprises a plurality of acoustic sources.

10. An apparatus according to claim 9, wherein the signal produced by the interaction with the sample is obtained by examination of the loading effect on the driving signal to the acoustic sources.

11. An apparatus according to claim 1, wherein the signal produced by the interaction with the sample is obtained by comparing the driving signal to the modulated signal received by one or more detectors.

12. An apparatus according to claim 1, wherein the liquid sample is in the form of a drop which is analysed statically for a fixed drop volume.

13. An apparatus according to claim 1, wherein the liquid drop undergoes a growth and release cycle, where one or more of a succession of drops are allowed to drip from the end of an acoustic drop head.

14. An apparatus according to claim 1, wherein the acoustic energy is selected from acoustic radiation which is pulsed, continuous, varying in frequency, amplitude or phase or otherwise modulated.

15. An apparatus according to claim 1, wherein the means for directing acoustic energy comprises an acoustic source, and a liquid sample separated from the source by an intervening medium.

16. An apparatus according to claim 15, wherein the acoustic energy is launched at the unattached surface of the sample through said medium.

17. An apparatus according to claim 16, wherein the means for deriving a signal related to the interaction of the acoustic energy with the liquid sample monitors two or more signals, including a signal which penetrates the sample, and a signal based on the acoustic field set up immediately outside of the sample.

18. An apparatus according to claim 1, wherein the means for deriving a signal related to the interaction of the acoustic energy with the liquid sample comprises an acoustic transduction measurement system.

19. An apparatus according to claim 18, wherein the transduction measurement system employs an electrical driving signal associated with a source transducer and an electrical modulated signal associated with a detector transducer, and wherein changes in the driving signal and the modulated signal are used to deduce properties relating to the liquid sample.

20. An apparatus according to claim 19, wherein a single transducer acts as both source transducer and detector transducer.

21. An apparatus according to claim 1, further comprising means for forcing movement or oscillation of the liquid sample during acoustic measurements.

22. An apparatus according to claim 1, further comprising a tube for containing the liquid sample, whereby the surface of the sample liquid is a meniscus within said tube.

23. A method for measuring a property of a liquid, energy at a sample of the liquid, modulating the acoustic energy being directed at the liquid independently of the resonant frequency of the sample, deriving a signal related to the interaction of the acoustic energy with the liquid sample as the acoustic energy is modulated, and providing an output indicative of a property of the liquid based upon the said signal, wherein the liquid sample is in the form of a drop which is analysed dynamically during a change in drop volume and wherein the output provides a characteristic measurement of the properties of the liquid over a range of volumes based on varying acoustic energy input parameters.

* * * * *